United States Patent [19]

Shiio et al.

[11] Patent Number: 5,077,207

[45] Date of Patent: Dec. 31, 1991

[54] PROCESS FOR THE PRODUCTION OF L-THREONINE BY FERMENTATION

[75] Inventors: Isamu Shiio, Kawasaki, Japan; Yasuhiko Toride, Bangkok, Thailand; Atsushi Yokota, Kawasaki, Japan; Shinichi Sugimoto, Kawasaki, Japan; Kazue Kawamura, Kawasaki, Japan

[73] Assignee: Ajinomoto Co., Inc., Tokyo, Japan

[21] Appl. No.: 299,653

[22] Filed: Jan. 23, 1989

[51] Int. Cl.$^5$ .................... C12P 13/08; C12N 15/00; C12N 1/20

[52] U.S. Cl. ................... 435/115; 435/172.1; 435/252.1; 435/840

[58] Field of Search .................. 435/115, 172.1, 840, 435/252.1

[56] References Cited

FOREIGN PATENT DOCUMENTS 59-45895 3/1984 Japan.

OTHER PUBLICATIONS

Stanbury et al., Principles of Fermentation Technology, 1984, pp. 40–42.
Goodfellow et al., "The Biology of the Actinomycetes", 1984, pp. 77–79.
Agric. Biol. Chem., vol. 43, No. 2, 1979, pp. 265–270; O. Tosaka et al.: "Mode of Conversion of asparto beta-semialdehyde to L-threonine and L-lysine in *Brevibacterium lactofermentum*".
Chemical Abstracts, vol. 93, 1980, p. 727, resume No. 6858t, Columbus, Ohio, U.S.; I. Murgov et al.: "Production of *Br. flavum* mutants Resistant to alpha-amino-beta-hydroxyvaleric Acid and Breeding of threonine Producers", & Nauchni Tr., Vissh Inst. Khranit. Vkusova Prom-St., Plovdiv 1978, 25, Pt. 2, 261–4.
Agric. Biol. Chem., vol. 42, No. 1, 1978, pp. 95–100; O. Tosaka et al.: "Pathway and regulation of lysine biosynthesis in *Brevibacterium lactofermentum*".
Biotechnology of Amino Acid Production, Progress in Industrial Microbiology, vol. 24, chapitre 15, 1986, pp. 173–182, Elsevier, Amsterdam, NL; S. Nakamori: "Threonine and homoserine".

*Primary Examiner*—Douglas W. Robinson
*Assistant Examiner*—Irene Marx
*Attorney, Agent, or Firm*—Oblon, Spivak, McClelland, Maier & Neustadt

[57] ABSTRACT

A process for the production of L-threonine, comprising cultivating a mutant bacterial species belonging to the genus Brevibacterium from which dihydrodipicolinate synthase has been deleted or removed in a liquid medium; accumulating the L-threonine as a product of cultivation; and harvesting the L-threonine from the culture medium.

3 Claims, No Drawings

PROCESS FOR THE PRODUCTION OF L-THREONINE BY FERMENTATION

BACKGROUND OF THE INVENTION

1. Field of the Invention

The present invention relates to a process for the production of L-threonine (hereinafter referred to as threonine) by a fermentation technique.

2. Description of the Background

Threonine is an important amino acid which is used in animal feeds and medicines. One process which is known for its production is a fermentation method. In this technique a mutant of the genus Brevibacterium having resistance to bacterial α-amino-β-hydroxyvaleric acid (hereinafter referred to as AHV) which is a threonine analog (Agric. Biol. Chem., 34 (3) 448–456 (1970), Japanese Patent Publication No. 26708/70) is cultured. This process employs as an AHV-resistant mutant, a strain having homoserine dehydrogenase (hereinafter referred to as HD) in which feedback inhibition due to threonine has been removed (J. Biochem., 68, 859–866 (1970)). The yield of threonin produced by this process is low, and therefore, it is not an economical method for the production of threonine which is added to animal feeds. Accordingly, in order to enhance the yield of threonine, a mutant which is frequently used is one which is a lysine-producing strain. However, in this case, lysine is frequently produced as a by-product, which adversely affects the yield of threonine. Further, the separation of lysine from the medium is a complicating factor. A need therefore continues to exist for a method of producing threonine in improved yields by a fermentation technique.

SUMMARY OF THE INVENTION

Accordingly, one object of the present invention is to provide a fermentation technique of producing L-threonine in enhanced quantities.

Briefly, this object and other objects of the present invention as hereinafter will become more readily apparent can be obtained by a method for the production of L-threonine by cultivating a mutant bacterial species belonging to the genus Brevibacterium from which dihydrodipicolinate synthase has been deleted or removed in a liquid medium; accumulating said L-threonine as a product of cultivation; and harvesting said L-threonine from said culture medium. The mutant strains are distinguished from other known bacteria by the fact that the feedback inhibition of HD because of threonine has not been removed.

DETAILED DESCRIPTION OF THE PREFERRED EMBODIMENTS

As will be evident from the description below, the yield of threonine obtained upon fermentation of the mutants used in the present process is more or less the same as the yields obtained upon fermentation of conventional threonine producing strains. Further, since DPS is the primary enzyme in the lysine biosynthetic pathway, if a mutant is produced in which it has been deleted or reduced, the amount of the lysine produced as a by-product may be decreased. Furthermore, since the mutant of the present invention is by nature completely different from conventional mutants employed, a possible way of enhancing the yield of threonine is to overlap it with a conventional strain.

The microorganism used in the process for the production of threonine in the present invention is a strain which belongs to the genus Brevibacterium in which DPS has been deleted or reduced. In addition to this feature, if the mutant is imparted with HD feedback inhibition removal, L-methionine auxothropy, L-isoleucine auxothropy, ethionine resistance, lysine analog resistance, pyruvate kinase deletion, and the like, the productivity of threonine may further be enhanced. The parent strain of the mutant of the present invention is a microorganism belonging to the genus Brevibacterium known as the so-called L-glutamic acid producing bacteria, and may be exemplified by the following strains:

| | |
|---|---|
| Brevibacterium flavum | ATCC 14067 |
| Brevibacterium divaricutum | ATCC 14020 |
| Brevibacterium lactofermentum | ATCC 13869 |
| Brevibacterium roseum | ATCC 13825 |

The mutant used in the present invention may be obtained by carrying out a mutation operation on the above-described parent strains, thereby effecting the deletion or reduction of DPS. The mutation operation may be conducted by a conventional method such as, for example, ultraviolet light irradiation, or chemical treatment using N-methyl-N'-nitro-N-nitrosoquanidine (hereinafter referred to as NG), nitrous acid, or the like. After the mutation operation, the DPS deleted or reduced mutant may be separated by selecting strains resistant to AHV which also produce threonine, and measuring the DPS activity of these strains. Especially, when a lysine-producing strain of a type in which synergistic inhibition of aspartokinase (hereinafter referred to as AK) due to threonine and lysine has been removed is used as the parent strain, by selecting the strain which produces less lysine by-product in comparison to the threonine yield among the AHV-resistant, threonine-producing strains obtained, it is possible to obtain the DPS deleted strain more efficiently.

A specific method for deriving Brevibacterium flavum AJ 12360 (FERM P-9821), which is an example of a strain useful in the present invention, is described below. The parent strain in the derivation process is the aspartic acid-producing strain AJ 11955 (FERM P-6665, Japanese Patent Application Laid-open No. 45895/84) which in turn is derived from Brevibacterium flavum AJ 14067. Brevibacterium flavum AJ 11955 was treated with 150 μg/ml of NG at 30° C. for 15 minutes. Then, a glucose minimum agar plate medium (9 cm in diameter) shown in Table 1 and also containing 10 g/l of AHV and 5 g/l of lysine was inoculated with the bacterium to give about $10^5$ cells per plate, and the colonies appearing after cultivation for 5 days were transferred to a complete agar plate medium shown in Table 2 as the resistant strains. Thereafter, a medium for threonine production shown in Table 3 was dispensed in 3 ml amounts into test tubes. (The medium contained 70 g/l of ammonium sulfate and 30 ml/l of soybean hydrolysate and is simply referred to as N70S30.) The media were inoculated with these strains, and the resulting cultures were agitated at 30° C. for 72 hours. Strains producing threonine were then selected. Of the mutant strains, strain AJ 12360, which exhibited the maximum productivity, was analyzed by the method described hereinbelow. It was found that the HD feedback inhibition of the strain was the same as the parent strain, but the DPS activity had been deleted (Table 4).

The following is a specific method for the derivation of DPS deleted or reduced strains AJ 12361-2 (FERM P-9822-3) obtained from lysine-producing *Brevibacterium flavum* AC 664 as the parent strain having AK in which synergistic inhibition due to threonine and lysine is removed. The AC 664 strain was treated with 600 μg/ml of NG at 30° C. for 15 minutes. Then, an acetic acid-pyruvic acid agar plate medium shown in Table 3 and containing 2-5 g/l of AHV was inoculated with the NG treated cells so as to give about $10^7$ cells per plate. Thereafter, the colonies appearing after cultivation for 12 days were transferred as the resistant strains. The threonine and lysine productivity of these strains was examined by the above-described cultivation method, except that a composition identified as N25S35 was used as the medium for threonine production. Five strains which yielded small amounts of lysine by-product in comparison to the yield of threonine produced were selected. Of the strains, as shown in Table 6, three identified as AJ 12361 and 12362 and DA 110, exhibited a feedback inhibition of HD which was the same as that of the parent strain, but the DPS activity had been deleted or reduced. The reason why the strains giving lower amounts of lysine by-product were selected is that since DPS is an enzyme which catalyzes the reaction of diaminopimelic acid (hereinafter referred to as DAP) in the lysine synthetic pathway, the amount of lysine produced is believed to be greatly reduced by using DPS deleted strains. In fact, with these 3 strains, as shown in Table 6, the lysine/threonine ratios were lower than the ratios obtained from AJ 12363 (FERM P-9824) which is a representative strain of the known threonine-producing strains derived from the same parent strain and having HD in which feedback inhibition due to threonine has been removed.

The amount of threonine produced in a given fermentation experiment was measured by the method described below, and the amount of lysine produced was measured by an acidic ninhydrin method. Further, the DPS activity was measured as follows. A medium obtained by adding 1 g/l of DAP to a medium useful for threonine production shown in Table 3 was dispensed in 20 ml amounts into 500 ml flasks which could be shaken. The flasks were sterilized by autoclaving. The medium compositions used were N50S30 for the AJ 12360 strain and N25S35 for the AJ 12361-2 and DA 110 strains. Each medium was inoculated with one loop of the strain which had been previously cultivated in a complete agar plate medium shown in Table 2. Each medium was supplemented with 1 g/l of DAP and 300 mg/l of L-histidine hydrochloride at 30° C. for 24 hours, and culturing was conducted at 30° C. for 40 hours in the shaking flasks. The cells were collected and washed with a 0.2% potassium chloride solution. These washed cells were suspended in a 50 mM potassium phosphate buffer (pH 7.0), and then were centrifugally separated after ultrasonic treatment in a supernatant. The supernatant was gel filtered through a Sephadex G25 column using the same buffer to prepare a crude enzyme solution. The activity was measured by carrying out the reaction at 30° C. for 10 minutes, terminating the reaction by adding 1 ml of 0.05 N hydrochloric acid thereto, and then measuring the change in absorbance at 340 nm by using a reaction mixture shown in Table 8 to determine the amount of pyruvic acid consumed. The control for this reaction was a DL-aspartate-β-semialdehyde-free system. The HD activity was measured as follows. The crude enzyme solution was prepared in a manner similar to that employed in the above-described DPS activity measurement, except that a 0.1 M potassium phosphate buffer containing 0.5 M potassium chloride (pH 7.0) was used as the buffer instead of the 50 mM potassium phosphate buffer. The activity measurement was conducted by measuring the reduction in absorbance at 340 nm in the reaction system shown in Table 9. The control for this reaction was a DL-aspartate-β-semialdehyde-free system.

Thereafter, the degrees of AHV resistance of DPS deleted strains AJ 12360 and AJ 12361 were compared against their parent strains. The degree of AHV resistance was determined by cultivating the strain in the complete agar plate medium shown in Table 2 which also contained 1 g/l of DAP, 50 ml/l of dipicolinic acid and further, in the case of AJ 12361 and its parent strain AC 664, 300 mg/l of L-histidine hydrochloride as a growth promoting substance, at 30° C. for 24 hours. The cells were then washed with the glucose minimum liquid medium shown in Table 10. The same medium dispensed in 3 ml into test tubes, was inoculated with the cells, and the inoculated media were cultured while being shaked for 24 hours. The absorbance of each medium was measured at 566 nm under conditions in which AHV was added or was not added to a given medium. To each glucose minimum liquid medium prepared were added, as growth promoting substances, 200 mg/l of L-histidine hydrochloride, in the case of AJ 12361 and AC 664 strains, and 500 mg/l each of DAP and lysine in the case of AJ 12360 and AJ 11955 strains. Especially, since DAP or DAP and lysine often promoted the growth of the DPS deleted or reduced strain, DAP was added to the liquid and plate media in the experiments described so far as needed. As shown in Table 11, growth inhibition of both DPS deleted strains was difficult to achieve because of AHV in comparison to the respective parent strains, and thus the strains acquired AHV resistance.

The culture medium used for threonine production is not particularly critical in achieving the results of the invention. Conventional media containing carbon sources, nitrogen sources, inorganic salts, and minor organic nutrients, if needed can be employed. Suitable carbon sources include carbohydrates such as glucose, fructose, or hydrolysates of starch, cellulose and the like, molasses, and the like; organic acids such as acetic acid, citric acid and the like; alcohols such as glycerin, ethanol and the like, and hydrocarbons such as normal paraffins, and the like. Suitable nitrogen sources include ammonium sulfate, urea, ammonium nitrate, ammonium phosphate, ammonium chloride, ammonia gas, and the like. Suitable inorganic salts include phosphates, magnesium salts, calcium salts, iron salts, manganese salts, other minor metal salts and the like as needed. The minor organic nutrients which may be present in appropriate amounts include amino acids, if there is auxotrophy, vitamins, fatty acids, organic basic substances, and the like. Further, as there is need, growth promoting substances such as amino acids, vitamins, Ajieki (registered trademark, soybean hydrolysate), yeast extract, peptone, casamino acids, and the like may be added. Especially, in the case of the DPS deleted or reduced strains, the addition of DAP or DAP and lysine often promote growth, to improve the results obtained.

The conditions of cultivation may be conventional with cultivation being conducted at a pH of 5-9 at a temperature of 20°-40° C. under aerobic conditions for 24-72 hours. During cultivation, if the pH drops, calcium carbonate, separately sterilized is added to the medium or a base such as ammonia water, ammonia gas, or the like is used to neutralize the medium. Further, where an organic acid is used as the carbon source, any increase in pH is neutralized with a mineral acid or an organic acid.

The separation and harvesting of threonine may be carried out in a conventional manner. The production of threonine is combined by measurement of the appropriate Rf value on thin layer chromatography. The biological activity value obtained by microbiological assay agrees that threonine is the authentic product. Quantitative analysis for threonine was conducted by a microbiological assay technique using *Leuconostoc mesenteroides* (ATCC 8042).

Brevibacterium flavum FERM-BP 2178 (FERM-P 6665) (AJ 11955) was originally deposited on Aug. 14, 1982 at the Fermentation Research Institute, Agency of Industrial Sciences and Technology, Ministry of International Trade and Industry (FRI), 1-3, Higashi 1-chome, Tsukuba-shi, Ibaragi-ken 305, Japan, and was accorded the FERM-P number indicated above. *Brevibacterium flavum* FERM-BP 2179 (FERM-P 9821) (AJ 12360), FERM-BP 2180 (FERM-P 9823) (AJ 12362) and FERM-BP 2181 (FERM-P 9824) (AJ 12363) were originally deposited on Jan. 18, 1988 at FRI, and were accorded the FERM-P numbers indicated above. The strains were then converted into deposits under the Budapest Treaty on Dec. 7, 1988, and were accorded the corresponding FERM-BP numbers.

*Brevibacterium flavum* FERM-BP 2186 (FERM-P 9822) (AJ 12361) was originally deposited on Jan. 18, 1988 at FRI, and was accorded the FERM-P number indicated above. The strain was then converted into a deposit under the Budapest Treaty on December 14, 1988 and was accorded the corresponding FERM-BP number.

Having now generally described this invention, a further understanding can be obtained by reference to certain specific examples which are provided herein for purposes of illustration only and are not intended to be limiting unless otherwise specified.

EXAMPLE 1

The medium for threonine production (N50S30) shown in Table 3 was dispensed in 20 ml amounts into 500 ml shaking flasks and then was sterilized by autoclaving. One loopful of DPS deleted strain AJ 12360 was inoculated into a medium and another medium was inoculated with its parent strain AJ 11955 which had been previously cultivated in the complete agar plate medium of Table 2 and also supplemented with 1 g/l of DAP and 50 mg/l of dipicolinic acid at 30° C. for 24 hours, respectively. The amounts of threonine produced in the respective media were 10.7 g/l and 0 g/l (below the detection limit).

EXAMPLE 2

A DPS deleted strain AJ 12361, DA 110, DPS reduced strain AJ 12362, the parent strain AC 664 and the conventional type producing strain AJ 12363 were cultivated in the same manner as in Example 1 except that as the medium for threonine production, the composition N25S35 was used and L-histidine hydrochloride was added in 300 mg/l to the complete medium. The amounts of threonine produced in the respective media were 9.0, 6.3, 6.2, 0, and 8.9 g/l.

TABLE 1

| Glucose Minimum Plate Medium Composition | |
|---|---|
| Glucose | 20 g/l |
| Ammonium sulfate | 10 g/l |
| $KH_2PO_4$ | 10 g/l |
| $MgSO_4.7H_2O$ | 0.4 g/l |
| $FeSO_4.7H_2O$ | 10 mg/l |
| $MnSO_4.4H_2O$ | 8.1 mg/l |
| Thiamine hydrochloride | 0.1 mg/l |
| Biotin | 0.3 mg/l |
| Agar | 20 g/l |
| pH 7.0 (NaOH) | |

TABLE 2

| Complete Agar Plate Medium Composition | |
|---|---|
| Polypeptone | 10 g/l |
| Yeast extract | 10 g/l |
| NaCl | 5 g/l |
| Glucose | 5 g/l |
| Agar | 20 g/l |
| pH 7.0 (NaOH) | |

TABLE 3

| Medium for Threonine Production | |
|---|---|
| Glucose | 100 g/l |
| Ammonium sulfate* | 70 g/l |
| $KH_2PO_4$ | 1 g/l |
| $MgSO_4.7H_2O$ | 0.4 g/l |
| $FeSO_4.7H_2O$ | 10 mg/l |
| $MnSO_4.4H_2O$ | 8.1 mg/l |
| Thiamine hydrochloride | 0.2 mg/l |
| Biotin | 0.3 mg/l |
| Soybean hydrolysate (Total nitrogen 32 g/l)* | 30 ml/l |
| pH 7.0 (NaOH) | |

When the composition contains 70 g/l of ammonium sulfate and 30 ml/l of soybean hydrolysate, it is designated as N70S30.

TABLE 4

| Dihydrodipicolinate Synthase and Homoserine Dehydrogenase Activity | | |
|---|---|---|
| Strain | Dihydrodipicolinate Synthase Activity* | Homoserine Dehydrogenase Feedback Inhibition (5)** |
| AJ 11955 (parent strain) | 63.6 | 98 |
| AJ 12360 (mutant) | 0 | 98 |

*nmol/min/mg protein
**Degree of inhibition in the presence of 1 mM threonine (%)

TABLE 5

| Acetic Acid - Pyruvic Acid Agar Plate Medium Composition | |
|---|---|
| Acetic acid | 5 g/l |
| Sodium pyruvate | 5 g/l |
| Ammonium sulfate | 5 g/l |
| $KH_2PO_4$ | 1 g/l |
| $MgSO_4.7H_2O$ | 0.4 g/l |
| $FeSO_4.7H_2O$ | 10 mg/l |
| $MnSO_4.4H_2O$ | 8.1 mg/l |
| Thiamine hydrochloride | 0.1 mg/l |
| Biotin | 0.5 mg/l |
| HEPES | 23.8 g/l |
| Growth promoting substances | * |
| Agar | 20 g/l |
| pH 7.0 (NaOH) | |

*Yeast extract 0.4 g/l, L-cystine and L-alanine 20 mg/l respectively. L-tryptophane, L-phenylalanine, L-tyrosine, L-lysine hydrochloride, L-methionine and L-arginine hydrochloride 300 mg/l respectively.

TABLE 6
Dihydrodipicolinate Synthase and Homoserine Dehydrogenase Activity and Lysine/Threonine Productivity Ratio

| | Dihydrodipicolinate Synthase Activity* | Homoserine Dehydrogenase Feedback Inhibition (%)** | Amount of Lysine Produced/Amount of Threonine Produced |
|---|---|---|---|
| AC 664 (Parent strain) | 75.4 | 98 | — |
| AJ 12361 (Mutant) | 0 | 98 | 0.6 |
| DA 110 (Mutant) | 0 | 98 | 0.4 |
| AJ12362 (Mutant) | 4.2 | 96 | 0.7 |
| AJ12363 (Mutant) | 59.4 | 16 | 1.4 |

*, **Same as in Table 4

TABLE 7
Composition of Reaction Solution for Measuring Dihydrodipicolinate Synthase

| | |
|---|---|
| Imidazole hydrochloric acid buffer (pH 7.4) | 50 mM |
| DL-Aspartate-$\beta$-semialdehyde (as L-form) | 2.5 mM |
| Sodium pyruvate | 2.5 mM |
| Crude enzyme solution | 0.1 ml |
| Total volume | 0.5 ml |

React at 30° C. for 10 minutes, and then add 1 ml of 0.05 N hydrochloric acid to terminate the reaction.

TABLE 8
Composition of Reaction Solution for Measuring Pyruvic Acid

| | |
|---|---|
| Tris hydrochloric acid buffer (pH 7.5) | 100 mM |
| NADH$_2$ | 0.15 mM |
| Lactate Dehydrogenase | 20 g |
| Reaction solution of Table 7 after termination of the reaction | 0.2 ml |
| Total volume | 2 ml |

TABLE 9
Composition of Reaction Solution for Measuring Homoserine Dehydrogenase

| | |
|---|---|
| Potassium phosphate buffer (pH 7.0) | 100 mM |
| DL-Aspartate-$\beta$-semialdehyde [L-form] | 0.2 mM |
| NADPH$_2$ | 0.1 mM |
| Crude enzyme solution | 30 μl |
| Total volume | 1.5 ml |

TABLE 10
Composition of Glucose Minimum Liquid Medium

| | |
|---|---|
| Glucose | 20 g/l |
| Ammonium sulfate | 10 g/l |
| KH$_2$PO$_4$ | 1 g/l |
| MgSO$_4$.7H$_2$O | 0.4 g/l |
| FeSO$_4$.7H$_2$O | 10 mg/l |
| MnSO$_4$.4H$_2$O | 8.1 mg/l |
| Thiamine hydrochloride | 0.1 mg/l |
| Biotin | 0.3 mg/l |
| Urea | 3 g/l |
| pH 7.3 (NaOH) | |

TABLE 11
Degree of AHV Resistant of DPS Deleted Strain

| Concentration of AHV Added (mg/ml) | Relative Degree of Growth (%)* | | | |
|---|---|---|---|---|
| | AJ 11955 (Parent strain) | AJ 12360 (Mutant) | AC 664 (Parent strain) | AJ 12361 (Mutant) |
| 0 | 100 | 100 | 100 | 100 |
| 200 | 25 | 46.7 | 8.6 | 105 |
| 500 | 9.5 | 42.6 | 6.7 | 65.8 |
| 1000 | 5.9 | 37.5 | 6.1 | 39.1 |

*The degree of growth in the AHV free section taken as 100%

Having now fully described the invention, it will be apparent to one of ordinary skill in the art that many changes and modifications can be made thereto without departing from the spirit or scope of the invention as set forth herein.

What is claimed as new and desired to be secured by Letters Patent of the United States is:

1. A process for the production of L-threonine, comprising:
    cultivating, in a liquid nutrient medium, a mutant bacterial strain selected from the group consisting of *Brevibacterium flavum* FERM BP-2179, FERM BP-2180, FERM BP-2186;
    accumulating said L-threonine as a product of cultivation; and
    harvesting said L-threonine from said culture medium.

2. The process of claim 1, wherein the cultivating of said strain occurs at a temperature of 20°–40° C. at a pH of 5–9 under aerobic conditions for 24–72 hours.

3. The process of claim 1, wherein said nutrient medium contains at least one member selected from the group consisting of a carbon source, a nitrogen source, an inorganic salt and minor organic nutrients.

* * * * *

UNITED STATES PATENT AND TRADEMARK OFFICE
CERTIFICATE OF CORRECTION

PATENT NO. : 5,077,207
DATED : December 31, 1991
INVENTOR(S) : Isamu Shiio et al.

It is certified that error appears in the above-identified patent and that said Letters Patent is hereby corrected as shown below:

On the title page:

The Foreign Application Priority Data has been omitted,

Should be, --January 21, 1988 [JP] JAPAN.......63-12779--.

Signed and Sealed this

Twenty-first Day of September, 1993

*Attest:*

BRUCE LEHMAN

*Attesting Officer*    *Commissioner of Patents and Trademarks*